(12) United States Patent
Somasundaram et al.

(10) Patent No.: US 9,863,952 B2
(45) Date of Patent: Jan. 9, 2018

(54) METHOD FOR THE DIAGNOSIS OF HIGHER- AND LOWER-GRADE ASTROCYTOMA USING BIOMARKERS AND DIAGNOSTIC KIT THEREOF

(75) Inventors: Kumaravel Somasundaram, Bangalore (IN); Paturu Kondaiah, Bangalore (IN); Vani Santosh, Bangalore (IN); Sridevi Hegde, Bangalore (IN); Alangar Sathyaranjandas Hegde, Bangalore (IN); Manchanahalli Rangaswamy Satyanarayana Rao, Bangalore (IN)

(73) Assignee: Council of Scientific & Industrial Research, New Delhi (IN)

( * ) Notice: Subject to any disclaimer, the term of this patent is extended or adjusted under 35 U.S.C. 154(b) by 316 days.

(21) Appl. No.: 12/935,568

(22) PCT Filed: Mar. 31, 2009

(86) PCT No.: PCT/IN2009/000214
§ 371 (c)(1),
(2), (4) Date: Sep. 29, 2010

(87) PCT Pub. No.: WO2009/122444
PCT Pub. Date: Oct. 8, 2009

(65) Prior Publication Data
US 2011/0027797 A1    Feb. 3, 2011

(30) Foreign Application Priority Data
Mar. 31, 2008   (IN) .............................. 843/DEL/2008

(51) Int. Cl.
*G01N 33/574* (2006.01)
(52) U.S. Cl.
CPC ................... *G01N 33/57407* (2013.01); *Y10T 436/143333* (2015.01)

(58) Field of Classification Search
None
See application file for complete search history.

(56) References Cited

U.S. PATENT DOCUMENTS

| 7,341,552 | B2 | 3/2008 | Zhang et al. | |
|---|---|---|---|---|
| 2001/0051344 | A1* | 12/2001 | Shalon et al. | 435/6 |
| 2008/0014579 | A1* | 1/2008 | Liu et al. | 435/6 |
| 2008/0182246 | A1* | 7/2008 | Wang et al. | 435/6 |

OTHER PUBLICATIONS

Baker. Journal of the National Cancer Institute, vol. 95, No. 7, Apr. 2, 2003.*
Slonin, Nature Genetics Supplement, vol. 32, Dec. 2002, pp. 502-508.*
Michiels et al. Lancet, 2005; 365:488-492.*
Enard et al (Science. 2002. Apr. 12; 296(5566):340-43).*
Cheung (Cold Spring Harbor Symposia Quant. Biol., vol LXVIII, 2003, 403-408).*
Chan, Drug Discovery and Development, Apr. 1 2006, pp. 1-4.*
Hoshikawa et al. Physiol Genomics, 2003, 12:209-219.*
Robinson, Margaret S., "Cloning of cDNAs Encoding Two Related 100-kD Coated Vesicle Proteins (α-Adaptins)," *J. Cell Biol.* (1989), 108(3):833-842, The Rockefeller University Press.
Waelter et al., "The Huntingtin Interacting Protein HIP1 is a Clathrin and α-Adaptin-Binding Protein Involved in Receptor-Mediated Endocytosis," *Hum. Mol. Gen.* (2001), 10(17):1807-1817, Oxford University Press.

* cited by examiner

*Primary Examiner* — Sarae Bausch
(74) *Attorney, Agent, or Firm* — DLA Piper LLP (US)

(57) ABSTRACT

Disclosed is a method of diagnosing the presence of higher grade astrocytoma/glioblastoma (GBM) or lower-grade astrocytoma (DA or AA) in a human subject using secreted or plasma membrane associated biomarkers, which involves the detection of the expression levels of said genes, alone or in combination, in either tumor tissue samples or body fluids and a diagnostic kit thereof.

2 Claims, 1 Drawing Sheet

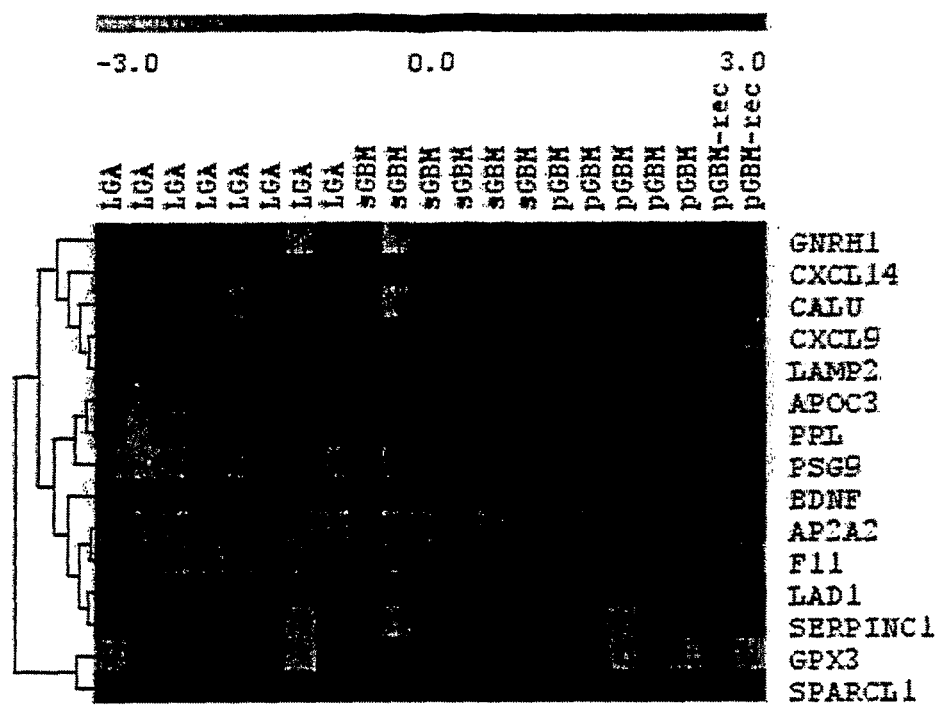

METHOD FOR THE DIAGNOSIS OF HIGHER- AND LOWER-GRADE ASTROCYTOMA USING BIOMARKERS AND DIAGNOSTIC KIT THEREOF

CROSS REFERENCE TO RELATED APPLICATIONS

This application is a 35 USC §371 National Stage application of International Application No. PCT/IN2009/000214 filed Mar. 31, 2009, now pending; which claims the benefit under 35 USC §119(a) to India Patent Application No. 843/DEL/2008 filed Mar. 31, 2008. The disclosure of each of the prior applications is considered part of and is incorporated by reference in the disclosure of this application.

FIELD OF THE INVENTION

The present invention relates to a method for diagnosing higher grade astrocytoma/glioblastoma or lower-grade, astrocytoma (DA or AA) using biomarkers.

More particularly, it relates to a diagnostic kit for detecting higher or lower-grade astrocytoma.

BACKGROUND AND PRIOR ART OF THE INVENTION

Gliomas are the most common primary brain tumors and occur at an incidence of almost 12 per 100,000 people (Landis S H, Murray T, Bolden S and Wingo P A. (1999). Cancer J. Clin., 49, 8-31). Diffuse astrocytoma may be classified (as per WHO classification) as low-grade diffuse (DA; Grade II), anaplastic (AA; Grade III) and glioblastoma (Grade IV; GBM), in the order of increasing, malignancy (Mischel P S and Vinters H V. (2001). (Ed. Liau, L.M.e.a.) Humana Press; Totowa, N.J., pp. 3-45). Currently, these classifications are based on the observed histopathological characteristics of the tumor, which are sometimes subjective and inconsistent. GBM constitutes more than 80% of malignant gliomas and patients with GBM have a median survival of less than one year. Current treatments, including surgery, radiation therapy, and chemotherapy, unfortunately have not changed the natural history of these incurable neoplasms; and the prognosis of patients with GBMs, has not improved significantly in the past 30 years (Davis F, Freels. S, Grutsch J, Barlas S and Brem S. (1998). J. Neurosurg., 88, 1-10). To find new diagnostic and therapeutic strategies, a better understanding of the biological pathway(s) leading to glial tumorigenesis is warranted.

Astrocytoma development is known to involve accumulation of a series of genetic alterations (Nagane M, Su Huang H J and Cavenee W K. (1997). Curr. Opin. Oncol., 9, 215-222) similar to other cancers. Identification of many of the genes involved in astrocytoma development, using standard molecular approaches, has helped to understand the process of astrocytoma genesis and progression (Louis D N and Gusella J F. (1995). Trends in Genetics, 11, 412-415). Frequent amplification of epidermal growth factor receptor (EGFR) (Hill J R, Kuriyama N, Kuriyama H and Israel M A. (1999). Arch. Neurol., 56, 439-441; Brock C S and Bower M. (1997). Medical Oncology, 14, 103-120), platelet derived growth factor receptor (PDGFR) (Hermanson M K, Funa M, Hartman L, Claesson-Welsh C H, Heldin B, Westermark and Nistér M. (1992). Cancer Res., 52, 3213-3219; Hermanson M, Funa K, Koopman J, Maintz D, Waha A, Westermark, B, Heldin, C H, Wiestler, O D, Louis D N, von Deimling A and Nistér M. (1996). Cancer Res, 56, 164-171; Maxwell M, Naber S P, Wolfe H J, Galanopoulos T, Hedley-Whyte E T, Black P and Antoniades N. (1990). J. Clin. Invest., 85, 131-40; Westermark B, Heldin C H, and Nistér M. (1995). Glia, 15, 257-263; Fleming T P, Saxena A, Clark W C, Robertson J T, Oldfield E H, Aaronson S A and Ali I U. (1992). Cancer Res., 52, 4550-4553), amplification of chromosome 12q region, which carries the cdk4 gene (Nagane M, Su Huang H J and Cavenee W K. (1997). Curr. Opin. Oncol., 9, 215-222; Hill J R, Kuriyama N, Kuriyama H and Israel M A. (1999). Arch. Neural., 56, 439-441) and alterations in chromosomes 1p, 9p, 10, 17p, 19q, and 22q have frequently been found in these tumors. In addition, mutations in the tumor suppressor gene p53 were found to be associated with chromosome 17p alterations in low grade and progressive astrocytoma (Maher E A, Furnari F B, Bachoo R M, Rowitch D H, Louis D N, Cavenee W K and DePinho R A. (2001). Genes Dev., 15, 1311-1333; Phatak P, Kalai Selvi S, Divya T, Hegde A S, Hegde S and Somasundaram K. (2002). J. Bioscience, 27, 673-686). Inactivation of the cdk inhibitor p16 INK4a residing in chromosome 9p, is very common in sporadic astrocytoma, occurring in 50-70% of high-grade gliomas and 90% of GBM cell lines (James C D, He J, Carlbom E, Nordenskjold M, Cavenee W K and Collins V P. (1991). Cancer Res., 51, 1684-1688; Olopade O I, Jenkins R B, Ransom D T, Malik K, Pomykala H, Nobori T, Cowan J M, Rowley J D and Diaz M O. (1992). Cancer Res., 52, 2523-2529). LOH in chromosome 10 is one of the most frequent alterations in GBM and is accompanied by the loss of PTEN/MMAC gene (Hill J R, Kuriyama N, Kuriyama H and Israel M A. (1999). Arch. Neurol., 56, 439-441).

Despite all this information about astrocytoma, our understanding of astrocytoma development is not sufficient enough to improve prognosis for GBM patients. A more global, systematic understanding of expression patterns of various genes and their downstream gene products in astrocytoma will hopefully provide new diagnostic and therapeutic targets. Towards this, a number of studies have reported the gene expression profile of astrocytoma (Liau L M, Lallone R L, Seitz R S, Buznikov A, Gregg J P, Kornblum H I, Nelson S F and Bronstein J M. (2000). Cancer Res., 60, 1353-1360; Sallinen S L, Sallinen P K, Haapasalo M K, Helin H J, Helen P T, Schraml P, Kallioniemi O P and Kononen J. (2000). Cancer Res., 60, 6617-6622; Rickman D S, Bobek M P, Misek D E, Kuick R, Blaivas M, Kurnit D M, Taylor J and Hanash S M. (2001). Cancer Res., 61, 6885-6891; Ljubimova J Y, Lakhter A J, Loksh A, Yong W H, Riedinger M S, Miner J H, Sorokin L M, Ljubimova A V and Black K L. (2001). Cancer Res., 61, 5601-5610; Watson M A, Perry A, Budhjara V, Hicks C, Shannon W D and Rich K M. (2001). Cancer Res., 61, 1825-1829; Tanwar M K, Gilbert M R and Holland E C. (2002). Cancer Res., 62, 4364-4368; Fathallah-Shaykh H M, Rigen M, Zhao L J, Bansal K, He B, Engelhard H H, Cerullo L, Von Roenn K, Byrne R, Munoz L, Rosseau G L, Glick R, Lichtor T and DiSavino E. (2002). Oncogene, 21, 7164-7174; Nutt C L, Math D R, Betensky R A, Tamayo P, Cairncross J G, Ladd C, Pohl U, Hartmann C, McLaughlin M E, Batchelor T T, Black P M, von Deimling A, Pomeroy S L, Golub T R and Louis D N. (2003). Cancer Res., 63, 1602-1607; Wang. H, Wang H, Shen W, Huang H, Hu L, Ramdas L, Zhou Y, Liao W S L, Fuller G N and Zhang. W. (2003). Cancer Res., 63, 4315-4321; Godard S, Getz G, Delorenzi M, Farmer P, Kobayashi H, Desbaillets I, Michimasa N, Diserens A C, Hamou M F, Dietrich P Y, Regli L, Janzer R C, Bucher P, Stupp R, de Tribolet N, Domany E and Hegi M E. (2003). Cancer Res., 63, 6613-6625).

It is also desirable to be able to target specific therapeutic modalities to pathogenically distinct tumor types to maximize efficacy and minimize toxicity to the patient. (Golub T R, Slonim D K, Tamayo P, Huard C, Gaasenbeek M, Mesirov J P, Coller H, Loh M L, Downing J R, Caligiuri M A, Bloomfield C D, Lander E S. (1999) *Science* 286, 531-37; Kleihues Kudoh K, Ramanna M, Ravatn R, Elkahloun A G, Bittner M L, Meltzer P S, Trent J M, Dalton W S, Chin K V. (2000) *Cancer Res.* 60(15), 4161-66). Previously, cancer classification has been based primarily on the morphological appearance of tumor cells. But this has serious limitations, because tumors with similar histopathological appearance can follow significantly different clinical courses and show different responses to therapy. For example, based on histopathological appearance, astrocytoma grade IV cannot consistently be distinguished from astrocytoma grade III.

Immunophenotyping for brain tumors has defined and refined diagnosis, e.g., distinguishing oligoastrocytoma from astrocytomas, and high-grade from low-grade astrocytomas. However, differential protein expression (GFAP, vimentin, synaptophysin, nestin) has not helped to improve therapeutic approaches. Prediction of transitions from low- to high-grade astrocytomas is difficult to make with currently available markers (De Girolami U, Cotran R C, Kumar V, Robbins S L. (1994) *Pathologic basis of disease,* 5th ed., W. B. Saunders Co., 1295-1357).

Zhang, J., Madden, T. L., (1997) *Genome Res.* 7(6), 649-56 (US Patent 20040053277) have identified a number of gene sets whose expression can accurately classify a glioma as glioblastoma (GBM), anaplastic astrocytoma (AA), anaplastic oligodendroglioma (AO) or oligodendroglioma (OL). Microarray gene expression profiling of glioma allows simultaneous analysis of thousands of genes and is likely to identify molecular markers associated with tumor grade, progression and survival. Through cDNA microarray experiments, we have identified genes which are differentially expressed between glioblastomas and lower-grade astrocytomas (grade II and grade III). Therefore, it is a desideratum to be able to diagnose the presence of astrocytoma and particularly its most malignant type i.e., glioblastoma and thus to be able to administer appropriate treatment. These and other benefits are provided by the present invention.

OBJECTS OF THE INVENTION

The main object of the present invention is to provide a method for diagnosing higher- and lower-grade astrocytoma using secreted and plasma membrane associated biomarkers Another object of the present invention is to provide a method for diagnosing glioblastoma or lower-grade astrocytoma (DA or AA).

Yet another object of the present invention is to provide biomarkers for diagnosing glioblastoma or lower-grade astrocytoma (DA or AA).

Another object of the present invention is to provide a diagnostic kit for detecting glioblastoma or lower-grade astrocytoma.

SUMMARY OF THE INVENTION

The present invention provides a system for identifying protein markers or a pattern of protein markers that indicate higher- and lower-Grade astrocytoma The present invention relates to a method of diagnosing glioblastoma or lower-grade astrocytoma based on the expression level of a single gene or combination of genes in a test sample of brain tissue cells or any body fluid obtained from the suspected subject and in a control sample of known normal subject, wherein higher level of expression of the gene in the test sample as compared to the normal sample, indicates glioblastoma or lower-grade astrocytoma in the subject from which the test sample has been obtained. It also relates to a diagnostic kit to detect and distinguish glioblastoma from lower-grade astrocytoma.

Accordingly the present invention provides a method of diagnosing higher and lower grade astrocytoma selected from a group consisting of glioblastoma or lower-grade astrocytoma in biological sample using secreted and plasma membrane associated isolated biomarkers, wherein the markers are genes selected from the group comprising AP2A2, APOC3, BDNF, CALU, CXCL14, CXCL9, F11, GNRH1, LAD1, LAMP2, PRL, PSG9, SERPINC1, GPX3, and SPARCL1.

In an embodiment of the present invention, the method of diagnosing the presence of higher grade astrocytoma also known as glioblastoma comprises determining the level of expression of a single or a combination of genes selected from the group comprising of AP2A2, APOC3, BDNF, CALU, CXCL14, CXCL9, F11, GNRH1, LAD1, LAMP2, PRL, PSG9 and SERPINC1 in a test sample obtained from said human subject and in a control sample of known normal human subject, wherein a higher level of expression of any of said genes in the test sample as compared to the control sample indicates the presence of glioblastoma in the human subject from which the test sample is obtained.

In another embodiment of the present invention, a method of diagnosing the presence of lower-grade astrocytoma comprises determining the level of expression of a single or both of the genes, GPX3 and SPARCL1 in a test sample obtained from said human subject and in a control sample obtained from known normal human subject, wherein a higher level of expression of GPX3 and SPARCL1 in the test sample, as compared to the control sample, indicates the presence of lower-grade astrocytoma in the human subject from which the test sample is obtained.

In yet another embodiment of the present invention, determining the level of expression of the said genes comprises determining the levels of the RNA transcripts of the said genes by employing an oligonucleotide in nucleic acid based detection methods.

In yet another embodiment of the present invention, the biological sample used is a brain tumor biopsy sample.

In yet another embodiment of the present invention, the biological sample comprises blood, plasma, serum, urine, cerebrospinal fluid, lymphatic fluid, pelvic; lavage, lung aspirate, nipple aspirate, breast duct lavage or any other body fluid.

In accordance with another aspect of the present invention, is provided a kit for diagnosing higher grade astrocytoma in a human subject, wherein the kit comprises:
a) Reagent capable of specifically detecting the level of expression of single or combination genes selected from the group comprising of AP2A2, APOC3, BDNF, CALU, CXCL14, CXCL9, F11, GNRH1, LAD1, LAMP2, PRL, PSG9 and SERPINC1.
b) Instructions for using said kit for characterizing higher grade astrocytoma in said human subject.

In still another embodiment of the present invention, the reagent in the kit stated above comprises a nucleic acid probe complementary to mRNAs of the said genes.

In still another embodiment of the present invention, the reagent in the kit comprises an antibody that specifically binds to proteins encoded by the said genes.

In accordance with another aspect of the present invention, is provided a kit for diagnosing lower-grade astrocytoma (DA or AA) in a human subject, wherein the kit comprises:

a) Reagent capable of specifically detecting the level of expression of single or both the genes, GPX3 and SPARCL1.

b) Instructions for using said kit for characterizing lower-grade astrocytoma in said human subject.

In still another embodiment of the present invention, the reagent in the kit stated above comprises a nucleic acid probe complementary to mRNAs of the said genes.

In still another embodiment of the present invention, the reagent in the kit stated above comprises an antibody that specifically binds to proteins encoded by the said genes.

In still another embodiment of the present invention, the kit is used for screening, detection, diagnosis, prognosis and as potential targets for higher grade astrocytoma and lower-grade astrocytoma (DA or AA).

In still another embodiment of the present invention, the kit is used for prognosis of higher grade astrocytoma and lower-grade astrocytoma (DA or AA).

In still another embodiment of the present invention, the subject used is a mammal.

In accordance with another aspect of the present invention is provided isolated bio marker useful for diagnosing higher and lower-grade astrocytoma in a subject wherein, the markers are genes selected from the group comprising AP2A2, APOC3, BDNF, CALU, CXCL14, CXCL9, F11, GNRH1, LAD1, LAMP2, PRL, PSG9, SERPINC1, GPX3, SPARCL1.

In yet another embodiment of the present invention is provided the use of biomarkers for screening, detection, prognosis and as potential targets for higher and lower-grade astrocytoma (DA or AA).

BRIEF DESCRIPTION OF THE DRAWINGS AND TABLES

FIG. 1. Heat map of SAM identified differentially regulated genes between glioblastoma and lower-grade astrocytoma.

Normalized, log 2-transformed expression ratios of SAM identified differentially regulated genes were visualized using a dual color code with red and green indicating up- and down-regulation respectively, in the particular glioma sample compared to normal brain tissue. Grey square represents the missing data. Data was subjected to hierarchical clustering using TMEV software to obtain better visualization. Thirteen genes are upregulated in GBMs as against lower-grade astrocytomas and two genes vice versa.

DETAILED DESCRIPTION OF THE INVENTION

The present invention relates to a method of diagnosing the presence of glioblastoma or lower-grade astrocytoma in a biological sample. Diffuse infiltrating astrocytomas include the following entities: 1. Diffuse astrocytoma (DA; WHO Gr. II), 2. Anaplastic astrocytoma (AA; WHO Gr. III) and 3. Glioblastoma (GBM; WHO Gr. IV).

The inventive method involves collecting or otherwise obtaining a test sample from suspected subject including of a bodily substance derived from the human subject, in which the sample contains human nucleic acid or protein originating from the subject, and quantitatively determining therein the level of expression of single or combination of genes selected from the group comprising of AP2A2, APOC3, BDNF, CALU, CXCL14, CXCL9, F11, GNRH1, LAD1, LAMP2, PRL, PSG9, SERPINC1, GPX3, SPARCL1. A characteristic higher expression of the any or a combination of the genes, AP2A2, APOC3, BDNF, CALU, CXCL14, CXCL9, F11, GNRH1, LAD1, LAMP2, PRL, PSG9 and SERPINC1, as compared to control sample from known healthy subject is diagnostic for the presence of glioblastoma, while the higher levels of GPX3 and/or SPARCL1 indicates the presence of lower-grade astrocytoma (see Table 1).

This includes detection by means of measuring of proteins or specific nucleic acids, such as RNA or cDNA. The sample is preferably collected directly from the human subject's body. Preferred and convenient substances for sampling include blood, lymph or plasma, serum, cerebrospinal fluid, other biopsy sample of cellular material from brain tissue. Cellular material includes any sample containing human cells, including samples of tissue, expressed tissue fluids (e.g., lymph or plasma) or tissue wash and the like. Tissue samples that can be collected include, but are not limited to, cell-containing material from the brain. This includes normal brain tissue, tumor tissue, tumor-adjacent tissue, and/or blood plasma from a site within the brain.

In accordance with the inventive methods, the tissue sample preferably contains cells that express a plurality of protein species and mRNA species, which proteins and/or mRNA species are detectably distinct from one another. "obtaining" and "collecting" the sample are used interchangeably herein and encompass sampling, resecting, removing from in situ, aspirating, receiving, gathering, and/or transporting the tissue sample or a concentrate, sediment, precipitate, supernatant, filtrate, aspirate, or other fraction of any of these. For example, conventional biopsy methods are useful for obtaining the tissue sample. These include percutaneous biopsy, laparascopic biopsy, surgical resection, tissue scrapes and swabs, sampling via stents, catheters, endoscopes, needles, surgical resection, and other known means. For example, to obtain a sample from inside the skull of the human subject; typically, Magnetic Resonance Imaging (MRI)-guided stereotactic techniques are employed, but other methods can be used.

The blood sample can be collected from subjects and is allowed to clot at room temperature for no more than 72 hrs, and then centrifuged at 4° C. for 5 min at 1000 rpm. The serum (upper phase) is separated and stored at −20° C. until use. The sample is alternatively derived from cultured human cells, cell-free extracts, or other specimens indirectly derived from a subject's body, as well as from substances taken directly from a subject's body. Samples may be stored before detection methods are applied (for example nucleic acid amplification and/or analysis, or immunochemical detection) by well known storage means that will preserve nucleic acids or proteins in a detectable and/or analyzable condition, such as quick freezing, or a controlled freezing regime, in the presence of a cryoprotectant, for example, dimethyl sulfoxide (DMSO), trehalose, glycerol, or propanediol-sucrose. Samples may also be pooled before or after storage for purposes of amplifying the nucleic acids specific for the said genes for analysis and detection, or for purposes of detecting the respective proteins.

The sample is used immediately or optionally pre-treated by refrigerated or frozen storage overnight, by dilution, by phenol-chloroform extraction, or by other like means, to remove factors that may inhibit various amplification reactions. The level of expression in the sample for the said proteins or their messenger ribonucleic acid (mRNA) is then detected quantitatively or semi-quantitatively.

Polynucleotides specific for the said genes, including mRNA species, are determined by base sequence similarity or homology to known nucleotide sequences. Base sequence homology is determined by conducting a base sequence similarity search of a genomics data base, such as the GenBank database of the National Center for Biotechnology Information (NCBI; www.ncbi.nlm.nih.gov/BLAST/), using a computerized algorithm, such as PowerBLAST, QBLAST, PSI-BLAST, PHI-BLAST, gapped or ungapped BLAST, or the "Align" program through the Baylor College of Medicine server (www.hgsc.bcm.tmc.edu/seq_data). (Altschul S F, Madden T L, Schaffer A A, Zhang 3, Zhang Z, Miller W, Lipman D J. *Nucleic Acids Res.* (1997) 25(17), 3389-402; Zhang, J., Madden, T. L., (1997) *Genome Res.* 7(6), 649-56; Madden T L, Tatusov R L, Zhang J. (1996) *Methods Enzymol.* 266, 131-41).

Preferably, polynucleotide sequences specific to the said genes, including an mRNA sequence, is at least 5 to 30 contiguous nucleotides long, more preferably at least 6 to 15 contiguous nucleotides long, and most preferably at least 7 to 10 contiguous nucleotides long. mRNA specific to any of the said genes can be, but is not necessarily, an mRNA species containing a nucleotide sequence that encodes a functional version of the said genes or fragments thereof. Also included among mRNAs specific to the said genes are splice variants.

Quantitative detection of levels of mRNAs specific to the said genes or their proteins, or of other proteins or mRNA, species of interest in accordance with the present invention is done by any known method that provides a quantitative determination of expression. A quantitative method can be absolute or relative. An absolute quantitation provides an absolute value for the amount or level of expression in comparison to a standard, which amount or level is typically a mole, mass, or activity value normalized in terms of a specified mass of protein, mass of nucleic acid, number or mass of cells, body weight, or the like. Additionally, the quantitative or absolute value is optionally normalized in terms of a specified time period, i.e., expression level as a rate. A relative detection method provides a unitless relative value for the amount or level of expression, for example, in terms of a ratio of expression in a given sample relative to a control, such as normal tissue or the expression of a selected "housekeeping" gene. The skilled artisan is aware of other examples of quantitative and semi-quantitative detection methods.

In accordance with the inventive methods, the expression level of the proteins encoded by the said genes is optionally detected by immunochemical means, such as, but not limited to, enzyme-linked immunosorbent assay (ELISA), immunofluorescent assay (IFA), immunoelectrophoresis, immunochromatographic assay or immunohistochemical staining, employing polyclonal or monoclonal antibodies or antibody fragments against the said gene products. Antibodies or antibody fragments that target the said proteins are available commercially or can be produced by conventional means.

Similarly, the expression levels of other proteins of interest, in accordance with the inventive methods, can be detected by conventional immunochemical means as described above. Most preferably, quantitative or semi-quantitative detection of the expression level of mRNA species is accomplished by any of numerous methods of nucleic acid amplification (e.g., amplification of specific nucleic acid segments) in the form of RNA or cDNA, which RNA or cDNA amplification product is ultimately measured after amplification. The final amplification product of RNA or cDNA is measured by any conventional means, such as, but not limited to, densitometry, fluorescence detection, or any other suitable biochemical or physical assay system. Before amplification, it is, preferable to extract or separate mRNA from genomic DNA in the sample and to amplify nucleic acids remaining in that fraction of the sample separated from the DNA, to avoid false positives that are caused by amplification of contaminating genomic DNA in the original specimen.

Histopathological means of classifying malignant tumors into grades are known for various kinds of malignant tumor, including astrocytomas. (Daumas-Duport C, Scheithauer B, O'Fallon J, Kelly P. (1988) *Cancer* 62, 2152-2165).

The present inventive method can be used to diagnose the presence of glioblastoma or lower-grade astrocytoma.

The foregoing descriptions of the methods of the present invention are only illustrative and by no means exhaustive. When these features of the present invention are employed, diagnostic and treatment decisions can be more appropriately optimized for the individual astrocytoma patient, and the prospects for his or her survival can be enhanced.

Identification of Differentially Regulated Genes Between Glioblastoma, and Lower-Grade Astrocytoma (DA and AA)

We obtained the expression profile of 18981 human genes using 19k cDNA microarrays (University Health Network, Canada) for twenty two samples of diffusely infiltrating astrocytoma comprising four diffuse astrocytoma (DA; Gr II), four AA (Gr. III) and fourteen GBM (Gr IV; six secondary and ten primary). Among the genes spotted on the microarray, 226 genes code for protein whose localization is either secreted or plasma membrane-associated. The expression data of these 226 genes was subjected to Significance Analysis of Microarrays using the two-class option to find out differentially regulated genes between lower-grade astrocytoma (DA/AA) and glioblastoma. While some of the found genes were already reported, some of them were novel. Of the found novel differentially regulated genes, two genes up regulated in LGA (DA/AA) as against GBM and thirteen genes are upregulated in GBM as against LGA (see FIG. 1).

EXAMPLES

The following examples are given by way of illustration of the present invention and therefore should not be construed to limit the scope of the present invention.

Example 1: Tissue Collection

Astrocytoma tissue samples were collected from patients, who underwent surgery at Sri Satya Sai Institute of Higher Medical Sciences and Manipal Hospital, Bangalore, India at the time of surgical resection. Controls comprised non-tumorous brain tissue samples (temporal lobe) collected from patients who underwent surgery for intractable epilepsy. A total of thirty-seven astrocytoma samples of different grades were used in this study. Tissues were bisected and one half was snap-frozen in liquid nitrogen and stored at −80° C. until RNA isolation. The other half was fixed in formalin and processed for paraffin sections and these were used to identify the histopathological grade and the type of astrocytoma.

TABLE 1

Diagnostic markers for Glioblastoma and Lower-Grade Astrocytoma

| SI No | Symbol | Gene Name | Protein localisation | LGA-Mean fold change* | GBM-Mean fold change* | Fold difference between GBM & LGA |
|---|---|---|---|---|---|---|
| Glioblastoma Specific Genes | | | | | | |
| 1 | AP2A2 NM_012305 | adaptor-related protein complex 2, alpha 2 subunit | Plasma membrane | −1.66 | 1.18 | 1.96 |
| 2 | APOC3 NM_000040 | apolipoprotein C-III | secreted | −1.46 | 1.08 | 1.58 |
| 3 | BDNF NM_170731 | brain-derived neurotrophic factor | secreted | −1.53 | −1.06 | 1.44 |
| 4 | CALU AL576538 | calumenin | secreted | 1.08 | 1.73 | 1.60 |
| 5 | CXCL14 KM_004887 | chemokine (C—X—C motif) ligand 14 | secreted | 1.03 | 1.59 | 1.55 |
| 6 | CXCL9 NM_002416 | chemokine (C—X—C motif) ligand 9 | secreted | 1.35 | 2.06 | 1.52 |
| 7 | F11 NM_J300128 | coagulation factor XI | secreted | −1.87 | 1.27 | 2.36 |
| 8 | GNRH1 NM_000825 | gonadotropin-releasing hormone 1 | secreted | 1.09 | 1.83 | 1.68 |
| 9 | LAD1 NM_005558 | ladinin 1 | secreted | −1.30 | 1.05 | 1.37 |
| 10 | LAMP2 MM_002294 | lysosomal-associated membrane protein 2 | Plasma membrane | 1.37 | 1.77 | 1.30 |
| 11 | PRL NM_000948 | prolactin | secreted | −1.44 | 1.23 | 1.77 |
| 12 | PSG9 MM_002784 | pregnancy specific beta-1-glycoprotein 9 | secreted | −2.14 | 1.15 | 2.46 |
| 13 | SERPINC1 NM_00048S | serine (or cysteine) proteinase inhibitor, clade C (antithrombin), member 1 | secreted | −1.13 | 1.41 | 1.58 |
| Lower-Grade Astrocytoma (DA and AA) Specific Genes | | | | | | |
| 14 | GPX3 NM_002084 | glutathione peroxidase 3 (plasma) | secreted | 2.83 | 1.04 | 2.73 |
| 15 | SPARCL1 NM_001128 310 | SPARC-like 1 (mast9, hevin) | secreted | 3.33 | −1.24 | 4.15 |

*fold change is calculated to w.r.t. normal brain

Example 2: RNA Isolation

Total RNA was extracted from the frozen tissue by a combination of the TRIzol method (Invitrogen, USA) and RNeasy Midi kit (Qiagen) according to the manufacturer's instructions. The RNA samples were quantified by measuring the absorbance using a spectrophotometer and visualized on a MOPS-Formaldehyde gel for quantity and quality assurance.

Advantages

It provides a useful method for diagnosing the presence of glioblastoma and low grade astrocytoma.
The method is useful both before and after clinical symptoms have appeared.
The method can also be applied to monitor the effectiveness of anti-cancer treatments.

REFERENCE

Altschul S F, Madden T L, Schaffer A A, Zhang J, Zhang Z, Miller W, Lipman D J. *Nucleic Acids Res.* (1997) 25(17), 3389-402.
Brock C S and Bower M. (1997). *Medical Oncology,* 14, 103-120.
Daumas-Duport C, Scheithauer B, O'Fallon J, Kelly P. (1988) *Cancer* 62, 2152-2165.
Davis F, Freels S, Grutsch J, Barlas S and Brem S. (1998). *J. Neurosurg.,* 88, 1-10.
De Girolami U, Cotran R C, Kumar V, Robbins'S L (1994) *Pathologic basis of disease,* 5th ed., W. B. Saunders Co., 1295-1357.
Fathallah-Shaykh H M, Rigen M, Zhao L J, Bansal K, He B, Engelhard H H, Cerullo L, Von Roenn K, Byrne R, Munoz L, Rosseau G L, Glick R, Lichtor T and DiSavino E. (2002). *Oncogene,* 21, 7164-7174.
Fleming T P, Saxena A, Clark W C, Robertson J T, Oldfield E H, Aaronson S A and Ali I U. (1992). *Cancer Res.,* 52, 4550-4553.
Godard S, Getz G, Delorenzi M, Farmer P, Kobayashi H, Desbaillets I, Michimasa N, Diserens A C, Hamou M F, Dietrich P Y, Regli L, Janzer R C, Bucher P, Stupp R, de Tribolet N, Domany E and Hegi M E. (2003). *Cancer Res.,* 63, 6613-6625.
Golub T R, Slonim D K., Tamayo P, Huard C, Gaasenbeek M, Mesirov J P, Coller H, Loh M L, Downing J R, Caligiuri M A, Bloomfield C D, Lander E S. (1999) *Science* 286, 531-37.
Hermanson M, Dina K, Koopman J, Maintz D, Waha A, Westermark, B., Heldin, C H, Wiestler, O D, Louis D N, von Deimling A and Nistér M. (1996). *Cancer Res.,* 56, 164-171.
Hermanson M K, Funa M, Hartman L, Claesson-Welsh C H, Heldin B, Westermark and Nistér M. (1992). *Cancer Res.,* 52, 3213-3219.
Hill J R, Kuriyama N, Kuriyama H and Israel M A. (1999). *Arch. Neurol.,* 56, 439-441.
James C D, He J, Caribom E, Nordenskjold M, Cavenee W K and Collins V P. (1991). *Cancer Res.,* 51, 1684-1688.
Kleihues Kudoh K, Ramanna M, Ravatn R, Elkahloun A G, Bittner M L, Meltzer P S, Trent J M; Dalton W S, Chin K V. (2000) *Cancer Res.* 60(15), 4161-66.
Landis S H, Murray T, Bolden S and Wingo P A. (1999). *Cancer J. Clin.,* 49, 8-31.
Liau L M, Lallone R L, Seitz R S, Buznikov A, Gregg J P, Kornblum H I, Nelson S F and Bronstein J M. (2000). *Cancer Res.,* 60, 1353-1360.
Ljubimova J Y, Lakhter A J, Loksh A, Yong W H, Riedinger M S, Miner J H, Sorokin L M, Ljubimova A V and Black K L. (2001). *Cancer Res.,* 61, 5601-5610.
Louis D N and Gusella J F. (1995). *Trends in Genetics,* 11, 412-415.

Madden T L, Tatusov R L, Zhang J. (1996) *Methods Enzymol.* 266, 131-41.

Maher E A, Furnari F B, Bachoo R M, Rowitch D H, Louis D N, Cavenee W K and DePinho R A. (2001). *Genes Dev.*, 15, 1311-1333.

Maxwell M, Naber S P, Wolfe H J, Galanopoulos T, Hedley-Whyte E T, Black P and Antoniades N. (1990). *J. Clin. Invest.*, 85, 131-40.

Mischel P S and Vinters H V. (2001). (Ed. Liau, L.M.e.a.) Humana Press; Totowa, N.J., pp. 3-45.

Nagane M, Su Huang H J and Cavenee W K. (1997). *Curr. Opin. Oncol.*, 9, 215-222.

Nutt C L, Mani D R, Betensky R A, Tamayo P, Cairncross J G, Ladd C, Pohl U, Hartmann C, McLaughlin M E, Batchelor T T, Black P M, von Deimling A, Pomeroy S L, Golub T R and Louis D N. (2003). *Cancer Res.*, 63, 1602-1607.

Olopade O I, Jenkins R B, Ransom D T, Malik K, Pomykala H, Nobori T, Cowan J M, Rowley J D and Diaz M O. (1992). *Cancer Res.*, 52, 2523-2529.

Phatak P, Kalai Selvi S, Divya T, Hegde A S, Hegde S and Somasundaram K. (2002). *J. Bioscience*, 27, 673-686.

Rickman D S, Bobek M P, Misek D E, Kuick R, Blaivas M, Kurnit D M, Taylor J and Hanash S M. (2001). *Cancer Res.*, 61, 6885-6891.

Sallinen S L, Sallinen P K, Haapasalo H K, Helin H J, Helen P T, Schraml P, Kallioniemi O P and Kononen J. (2000). *Cancer Res.*, 60, 6617-6622.

Tanwar M K, Gilbert M R and Holland E C. (2002). *Cancer Res.*, 62, 436-44368.

Wang H, Wang H, Shen W, Huang H, Hu L, Ramdas L, Zhou Y, Liao W S L, Fuller G N and Zhang W. (2003). *Cancer Res.*, 63, 4315-4321.

Watson M A, Perry A, Budhjara V, Hicks C, Shannon W D and Rich K M. (2001). *Cancer Res.*, 61, 1825-1829.

Westermark B, Heldin C H, and Nistér M. (1995). *Glia*, 15, 257-263.

Zhang, J., Madden, T. L., (1997) *Genome Res.* 7(6), 649-56.

We claim:

1. A method comprising:
   obtaining brain tissue from a subject having higher grade or lower grade astrocytoma;
   determining an expression level of a protein encoded by AP2A2 in the brain tissue obtained from the subject having higher grade or lower grade astrocytoma, wherein the expression level of protein is detected by ELISA;
   and administering a treatment to the subject having a higher grade or lower grade astrocytoma.

2. The method of claim 1, wherein protein is extracted from the brain tissue before determining the expression level of the protein encoded by AP2A2.

* * * * *